(12) United States Patent
Kreuder et al.

(10) Patent No.: US 6,329,082 B1
(45) Date of Patent: **\*Dec. 11, 2001**

(54) HETERO-SPIRO COMPOUNDS AND THEIR USE AS ELECTROLUMINESCENCE MATERIALS

(75) Inventors: Willi Kreuder, Mainz; Donald Lupo, Frankfurt; Josef Salbeck, Kelkheim; Hermann Schenk, Hofheim; Thomas Stehlin, Kriftel, all of (DE)

(73) Assignee: Hoechst Aktiengesellschaft, Frankfurt am Main (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/836,956
(22) PCT Filed: Nov. 22, 1995
(86) PCT No.: PCT/EP95/04593
§ 371 Date: May 22, 1997
§ 102(e) Date: May 22, 1997
(87) PCT Pub. No.: WO96/17035
PCT Pub. Date: Jun. 6, 1996

(30) Foreign Application Priority Data

Nov. 25, 1994 (DE) .................................................. 44 42 050

(51) Int. Cl.[7] ............................. H05B 33/14; C09K 11/06
(52) U.S. Cl. .................... 428/690; 428/917; 313/504; 252/301.16; 556/81; 556/87; 556/400; 556/406; 556/407; 556/426
(58) Field of Search ................................. 428/690, 691, 428/917; 315/504–509; 252/583, 301.16; 556/81, 87, 400, 406, 407, 410, 426, 465

(56) References Cited

U.S. PATENT DOCUMENTS 5,545,834 * 8/1996 Singh et al. ............................. 544/6
5,621,131 * 4/1997 Kreuder et al. ........................ 558/46
5,763,636 * 6/1998 Kreuder et al. ........................ 528/46

FOREIGN PATENT DOCUMENTS

0676461A2   10/1995   (EP).
WO 90/13148   11/1990   (WO).

OTHER PUBLICATIONS

J.M. Tour et al., J. Am. Chem. Soc., vol. 113, No. 18, 1991, pp. 7064–7066, (no month).

J.M. Tour et al., Polym. Prepr., 1990, pp. 408–409, (no month).

J.M. Tour et al., J. Am. Chem. Soc., vol. 112, No. 14, 1990, pp. 5662–5665, (no month).

* cited by examiner

Primary Examiner—Marie Yamnitzky
(74) Attorney, Agent, or Firm—Frommer Lawrence & Haug LLP

(57) ABSTRACT

Hetero-spiro compounds of the formula (I),

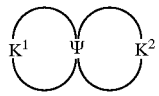

(I)

where $\Psi$ is an element of the 4th main group of the Periodic Table with the exception of carbon, preferably Sn, Ge or Si, particularly preferably Ge or Si, and $K^1$ and $K^2$ are, independently of one another, conjugated systems, for use in electroluminescence devices. The compounds of the formula (I) have a good solubility in customary organic solvents, improved film-forming properties and a significantly reduced tendency to crystallize.

23 Claims, No Drawings

HETERO-SPIRO COMPOUNDS AND THEIR USE AS ELECTROLUMINESCENCE MATERIALS

DESCRIPTION

There is a great industrial need for large-area solid-state light sources for a series of applications, predominantly in the field of display elements, VDU technology and lighting engineering. The demands made of these light sources can at present not be completely satisfactorily met by any of the existing technologies.

As an alternative to the conventional display elements, such as incandescent lamps, gas-discharge lamps and non-self-illuminating liquid crystal display elements, knowledge has existed for some time of electroluminescence (EL) materials and devices, such as light-emitting diodes (LEDs).

Electroluminescence materials are materials which are capable of radiating light on application of an electric field. The physical model for describing this effect is based on the radiative recombination of electrons and electron gaps (holes). In light-emitting diodes, the charge carriers are injected via the cathode or anode into the electroluminescence material. Electroluminescence devices comprise a luminescence material as light-emitting layer. Electroluminescence materials and devices are generally described, for example, in Ullmann's Encyclopedia of Industrial Chemistry, Vol A9, 5th Ed. VCH Verlag 1987 and the literature cited therein. Apart from inorganic materials, such as ZnS/Mn or GaAs, organic compounds have also become known as EL materials. A description of EL devices comprising low molecular weight organic EL materials is given, for example, in U.S. Pat. No. 4,539,507.

Disadvantages of these low molecular weight organic materials are, for example, the unsatisfactory film-forming properties and a pronounced tendency to crystallize.

Recently, polymers have also been described as EL materials (see, for example, WO-A 90/13148). However, the light yield (quantum efficiency) of these materials is considerably lower than for low molecular weight compounds.

It was desirable to find EL materials which have good light yields, at the same time can be processed into thin homogeneous films and have a low tendency to crystallize.

It has now surprisingly been found that hetero-spiro compounds have excellent suitability as EL materials. Spiro compounds have at least one tetravalent Spiro atom which links two ring systems to one another. This is described in detail in Handbook of Chemistry and Physics, 62nd edition (1981–2), pp. C-23 to 25.

Individual compounds of this type are described, for example, in U.S. Pat. No. 5,026,894, J. M. Tour et al., J. Am. Chem. Soc. 112 (1990) 5662 and J. M. Tour et al., Polym. Prepr. (1990) 408 as linkage elements for polymeric, organic semiconductors and have been proposed as materials for molecular electronics. However, possible use as EL materials cannot be derived therefrom.

The invention accordingly provides for the use of hetero-spiro compounds of the formula (I),

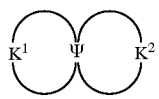

(I)

where $\Psi$ is an element of the 4th main group of the Periodic Table with the exception of carbon, preferably Sn, Ge or Si, particularly preferably Ge or Si, and $K^1$ and $K^2$ are, independently of one another, conjugated systems, in electroluminescence devices.

Compounds of the formula (I) have good solubility in customary organic solvents, improved film-forming properties and a significantly reduced tendency to crystallize. This makes the production of electroluminescence devices easier and increases their life. The emission properties of the compounds used according to the invention can be adjusted across the entire range of the visible spectrum by selection of suitable substituents. In addition, the covalently bound arrangement of the two parts of the spiro compound allows a molecular structure such that certain properties can be set independently in the two halves of the molecule. Thus, one half can have, for example, charge transport or charge injection properties, while the other half has light-emitting properties. The spatial proximity of the two halves fixed by the covalent linkage is here favorable for energy transmission (see, for example, B. Liphardt, W. Lüttke, Liebigs Ann. Chem. 1981, 1118).

Preferred compounds of the formula (I) are hetero-spiro compounds of the formula (II),

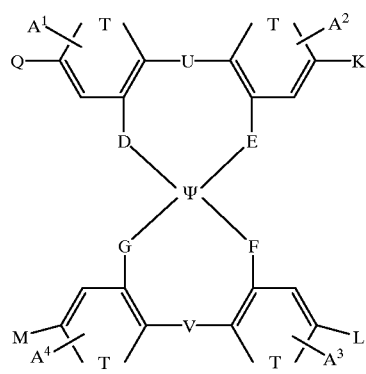

(II)

where the symbols and indices have the following meanings:

gs:

$\Psi$ is Si, Ge, Sn;

D, E, F, G are identical or different and are —$CR^1R^2$—, —O—, —S—, —$NR^3$— or a chemical bond;

U, V are identical or different and are —$CR^1R^2$—, —O—, —S—, —$NR^3$—, —$SiR^1R^2$—, —$SO_2$—, —CO—, —$CR^4$=$CR^5$— or a chemical bond, with the proviso that either U or V is —$CR^1$=$CR^2$— or a chemical bond;

T is —O—, —S—, —NR3—, —$CR^1R^2$—, —CH=N—, —$CA^5$=$CA^6$—, —CH=$CA^7$—, preferably —CH=CH—;

K, L, M, Q are identical or different, cyclic or acyclic hydrocarbon radicals which have conjugated electron systems and can also contain heteroatoms such as oxygen, nitrogen and/or sulfur;

$A^1$, $A^2$, $A^3$, $A^4$ can be identical or different and have the same meanings as K, L, M, Q or are hydrogen, fluorine or a hydrocarbon radical having from 1 to 22, preferably from 1 to 15, carbon atoms which can also contain heteroatoms such as oxygen, nitrogen, silicon or fluorine; preferably a linear, branched and/or ring-containing alkyl, alkoxy, or alkyloxycarbonyl group, —$CF_3$, —CN, —$NO_2$, —$NR^6R^7$, —Ar or —O—Ar;

$A^6$ is hydrogen $A^5$ and $A^7$ are identical or different and are the values for B herein defined below with respect to formula (IV).

$R^1$, $R^2$, $R^3$ are identical or different and are H or a hydrocarbon radical having from 1 to 12 carbon atoms, where $R^1$ and $R^2$ can together also form an unsubstituted or substituted ring;

$R^4$, $R^5$ are identical or different and have the same meanings as $R^1$, $R^2$, $R^3$ or are fluorine or —$CF_3$;

$R^6$, $R^7$ are identical or different and are H or a hydrocarbon radical having from 1 to 22 carbon atoms which can be aliphatic or aromatic, linear or branched and can also contain alicyclic elements, preferably methyl, ethyl, t-butyl, cyclohexyl, 3-methylphenyl; or $R^6$ and $R^7$ together form a ring,

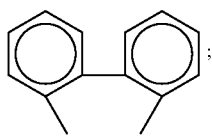

Ar is an aromatic radical having up to 22 carbon atoms, preferably phenyl, biphenyl, 1-naphthyl, 2-naphthyl, 2-thienyl, 2-furanyl, where each of these aromatic radicals can be substituted by one or two groups $R^4$, $R^5$;

Q and $A^1$, K and $A^2$, L and $A^3$, M and $A^4$ can, independently of one another, also each be joined together to form a ring which can be saturated, partially unsaturated or have maximum unsaturation, with a fused aromatic ring system preferably being present.

Particular preference is given to hetero-spirobifluorene derivatives of the formula (III),

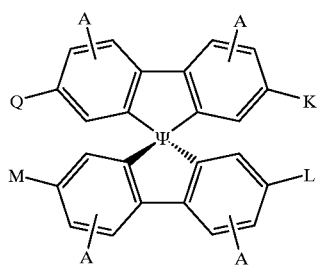
(III)

where the symbols and indices have the following meanings:

Ψ is Si or Ge;

K, L, M, Q, A are identical or different and are

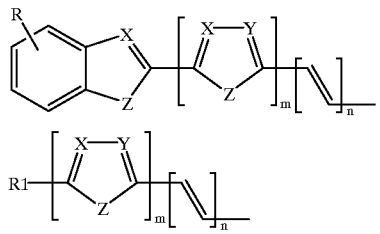

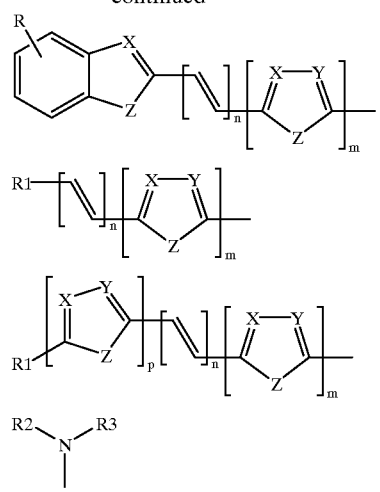

and A can also be identical or different and have the same meanings as R;

R can be identical or different and have the same meanings as K, L, M, Q or is —H, a linear or branched alkyl, alkoxy or ester group having from 1 to 22, preferably from 1 to 15, particularly preferably from 1 to 12, carbon atoms, —CN, —$NO_2$, —$NR^2R^3$, —Ar or —O—Ar;

Ar is phenyl, biphenyl, 1-naphthyl, 2-naphthyl, 2-thienyl, 2-furanyl, where each of these groups can bear one or two radicals R, m, n, p are, independently of one another, identical or different and are 0, 1, 2 or 3;

X, y are identical or different and are CR, N;

Z is —O—, —S—, —$NR^1$—, -$CR^1R^4$—, —CH=CH—, —CH=N—;

$R^1$, $R^4$ can be identical or different and have the same meanings as R;

$R^2$, $R^3$ are identical or different and are H, a linear or branched alkyl group having from 1 to 22 carbon atoms, —Ar, 3-methylphenyl.

Preferred compounds of the formula (III) are those of the formulae (IIIa)–(IIIg)

IIIa) K=L=M=Q and are selected from the group consisting of:

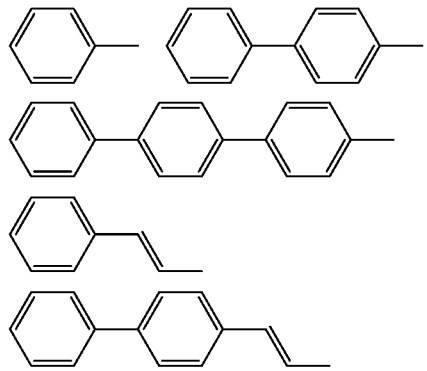

-continued
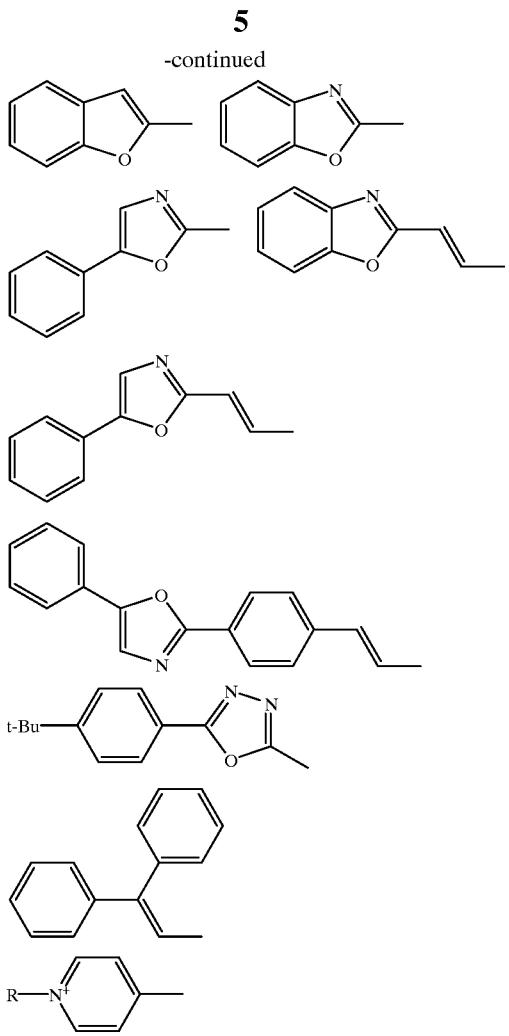
$R = C_1-C_{22}$-alkyl, $(CH_2)_x-SO_3^-$ where x=2, 3 or 4
IIIb) K=M=H and Q=L and are selected from the group consisting of:
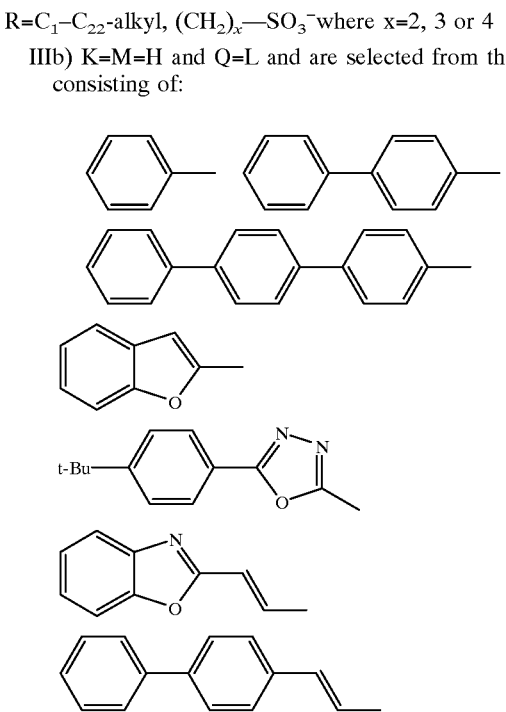
-continued
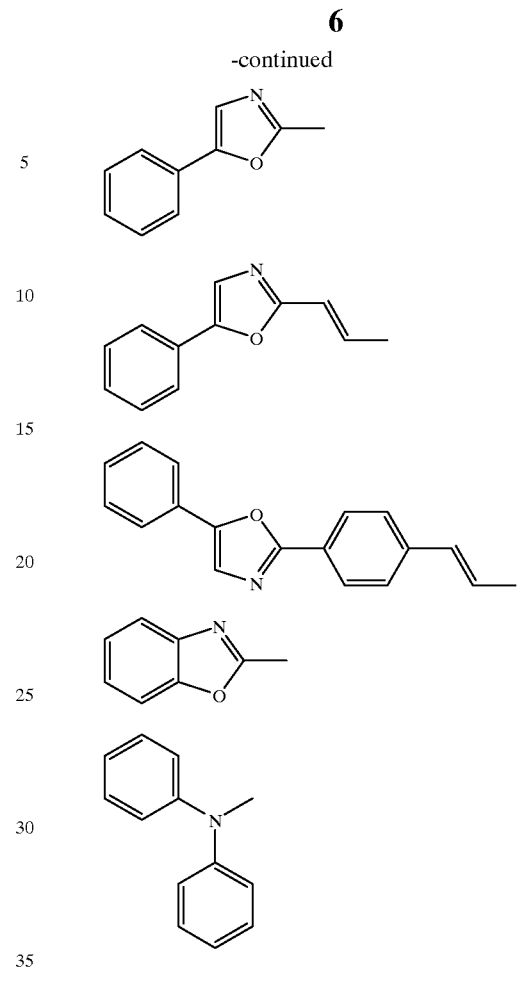
IIIc) K=M and are selected from the group consisting of:
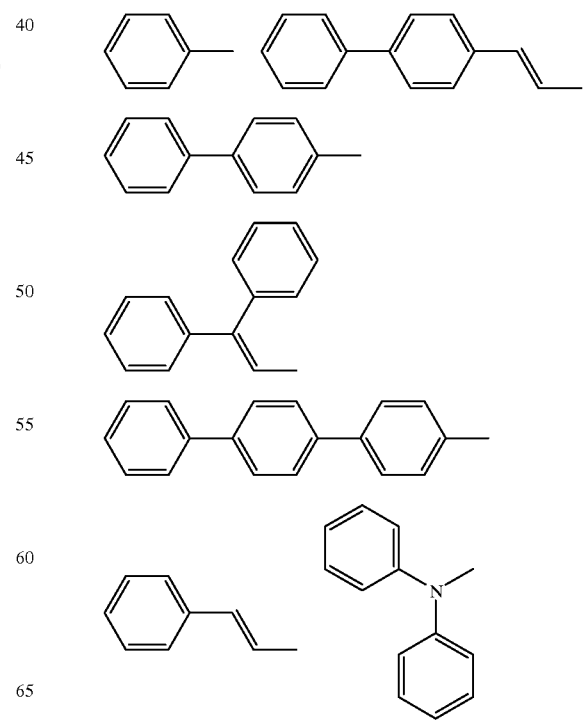

-continued
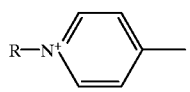
R=$C_1$–$C_{22}$-alkyl, $(CH_2)_x$—$SO_3^-$ where x=2, 3 or 4 and Q=L and are selected from the group consisting of:
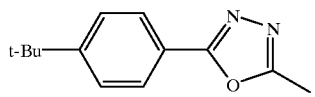
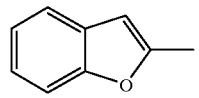
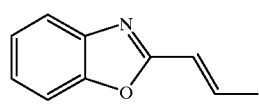
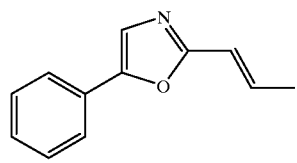
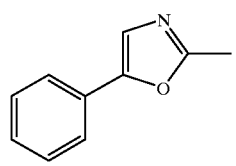
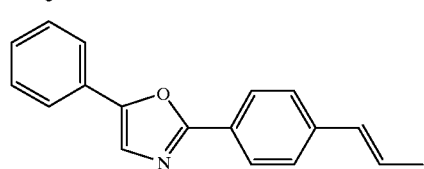
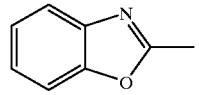
IIId) K=M and are selected from the group consisting of:
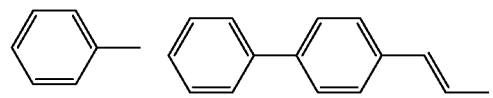
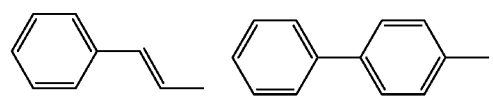
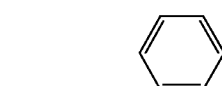
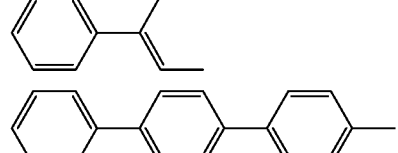
and Q=L and are selected from the group consisting of:
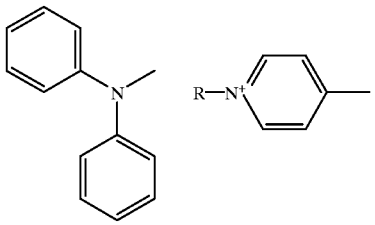
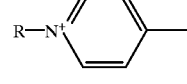
R=$C_1$–$C_{22}$-alkyl, $(CH_2)_x$—$SO_3^-$ where x=2, 3 or 4
IIIe) K=L=H and M=Q and are selected from the group consisting of:
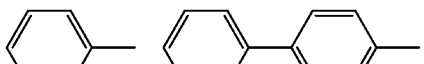
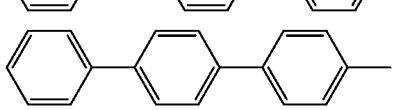
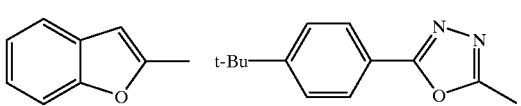
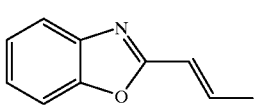
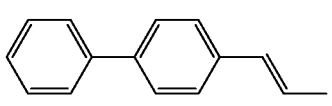
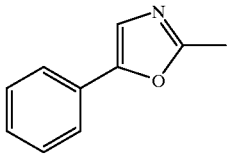
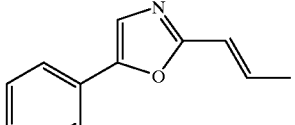
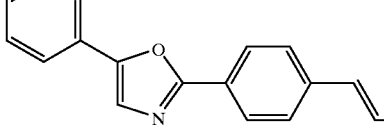
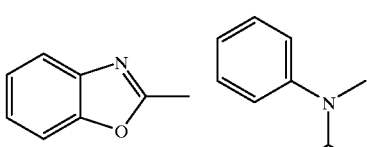

IIIf) K=L and are selected from the group consisting of:

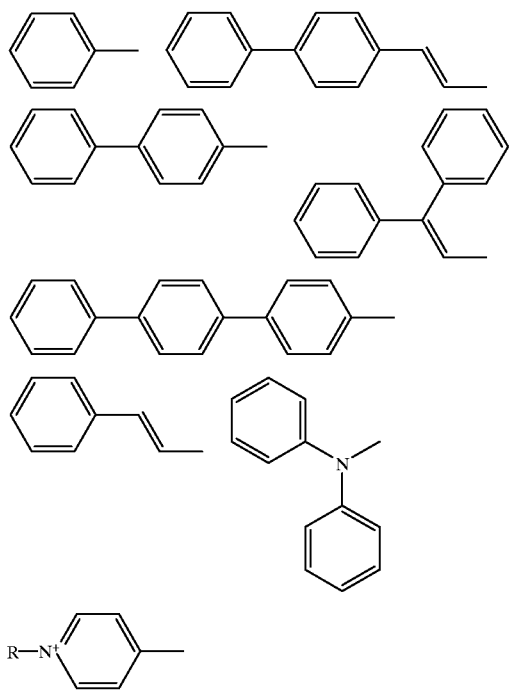

$R=C_1–C_{22}$-alkyl, $(CH_2)_x—SO_3^-$ where x=2, 3 or 4 and M=Q and are selected from the group consisting of:

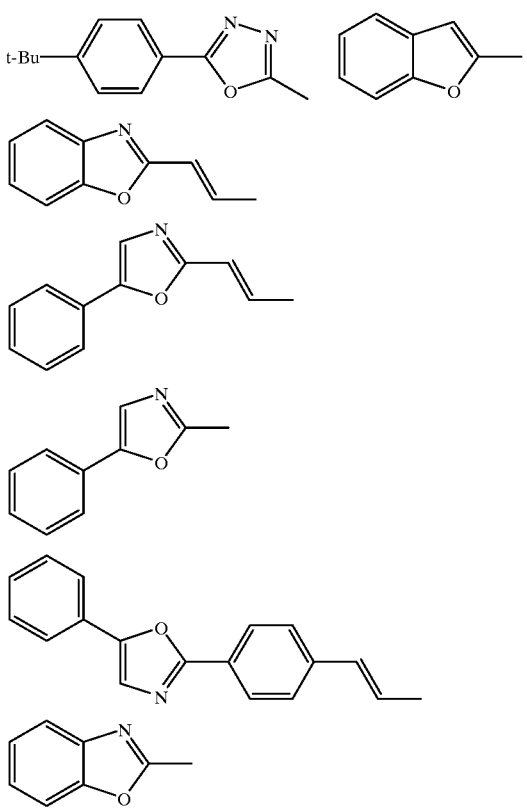

IIIg) K=L and are selected from the group consisting of:

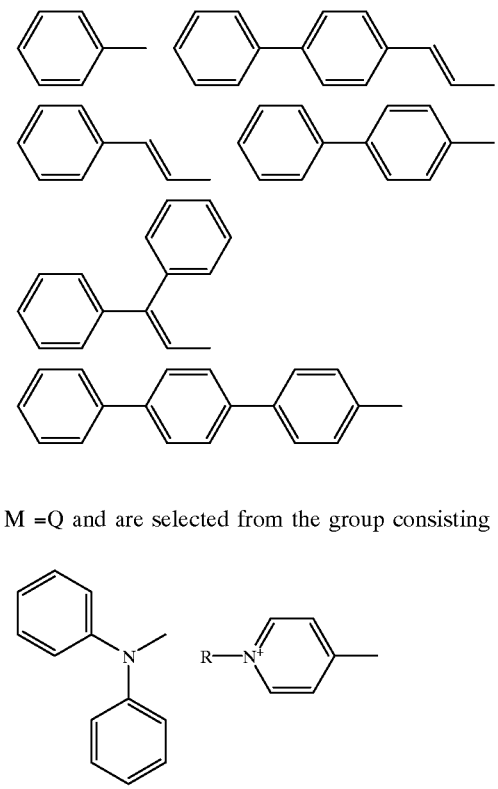

and M=Q and are selected from the group consisting of:

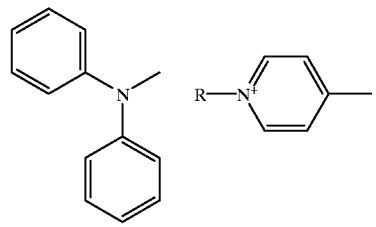

$R=C_1–C_{22}$-alkyl, $(CH_2)_x—SO_3^-$ where x=2, 3 or 4 particularly preferred compounds of the formula (III) are those of the formulae (IIIaa) to (IIIbd):

(IIIaa) K=L=M=Q and are selected from the group consisting of:

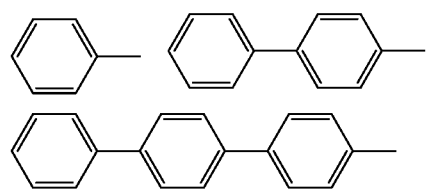

(IIIab) K=M=H and Q=L and are selected from the group consisting of:

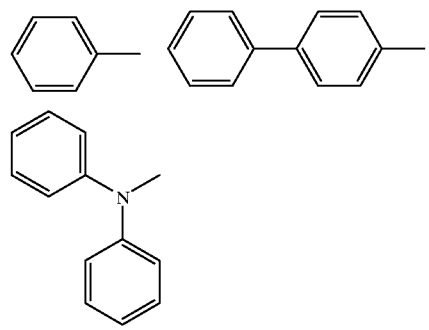

-continued

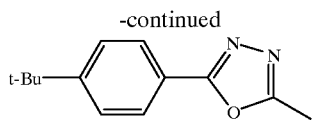

(IIIac) K=M and are selected from the group consisting of:

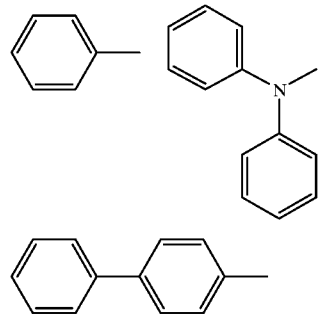

and Q = L and are:

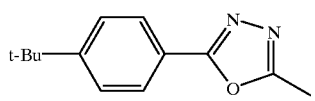

(IIIad) K=M and are selected from the group consisting of:

(IIIba) K=L=M=Q and are selected from the group consisting of;

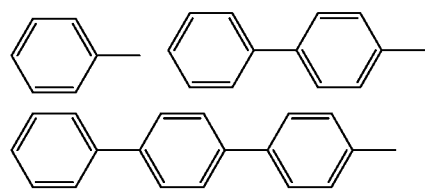

(IIIbb) K=L=H and M=Q and are selected from the group consisting of:

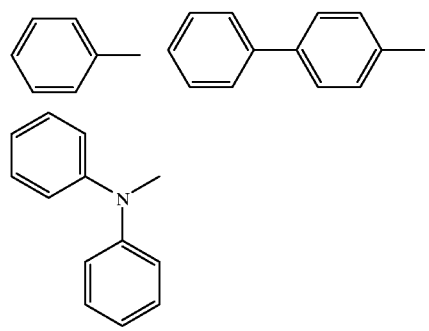

-continued

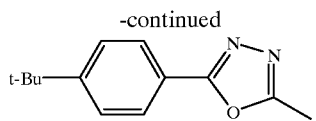

(IIIbc) K=L and are selected from the group consisting of:

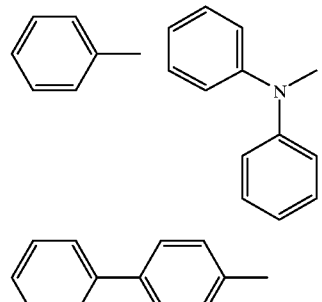

and M= Q and are:

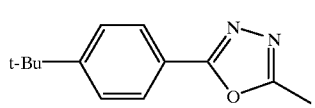

(IIIbd) K=L and are selected from the group consisting of:

and M = Q and are:

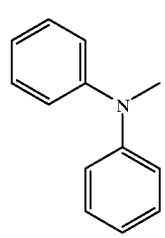

Very particularly preferred hetero-spiro compounds of the formula (III) are spirobi-9-silafluoreneg, such as 2,2',4,4',7,7'-hexakis (biphenylyl) -9,9'-spirobi-9-silafluorene,2,2',4,4',7,7'-hexakis (terphenylyl)-9,9'-spirobi-9-silafluorene, and also the compounds shown in Table 1 in which the abbreviations G1 to G14 denote the following structural elements:

G1

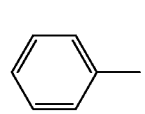

G2

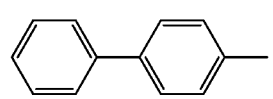

G3

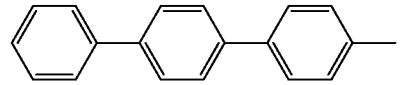

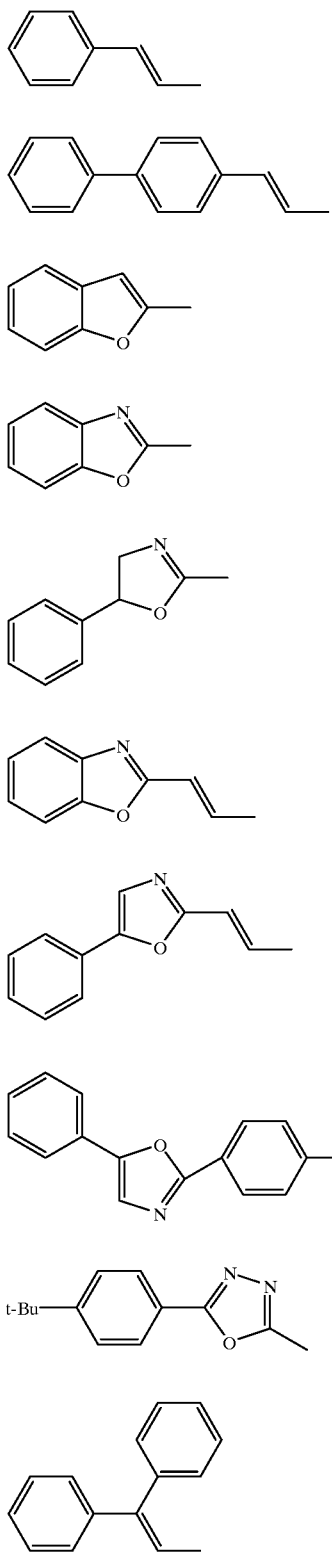
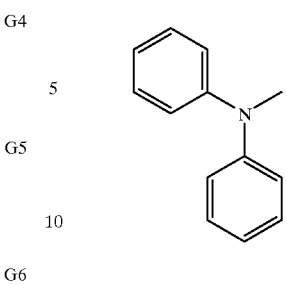

TABLE 1

Spirobi-9-silafluorene derivatives

| Compound | K | L | M | Q |
|---|---|---|---|---|
| Spiro-1 | G1 | G1 | G3 | G3 |
| Spiro-2 | G1 | G1 | G4 | G4 |
| Spiro-3 | G1 | G1 | G5 | G5 |
| Spiro-4 | G1 | G1 | G6 | G6 |
| Spiro-5 | G1 | G1 | G7 | G7 |
| Spiro-6 | G1 | G1 | G8 | G8 |
| Spiro-7 | G1 | G1 | G9 | G9 |
| Spiro-8 | G1 | G1 | G10 | G10 |
| Spiro-9 | G1 | G1 | G11 | G11 |
| Spiro-10 | G1 | G1 | G12 | G12 |
| Spiro-11 | G1 | G1 | G13 | G13 |
| Spiro-12 | G1 | G1 | G14 | G14 |
| Spiro-13 | G2 | G2 | G2 | G2 |
| Spiro-14 | G2 | G2 | G3 | G3 |
| Spiro-15 | G2 | G2 | G4 | G4 |
| Spiro-16 | G2 | G2 | G5 | G5 |
| Spiro-17 | G2 | G2 | G6 | G6 |
| Spiro-18 | G2 | G2 | G7 | G7 |
| Spiro-19 | G2 | G2 | G8 | G8 |
| Spiro-20 | G2 | G2 | G9 | G9 |
| Spiro-21 | G2 | G2 | G10 | G10 |
| Spiro-22 | G2 | G2 | G11 | G11 |
| Spiro-23 | G2 | G2 | G12 | G12 |
| Spiro-24 | G2 | G2 | G13 | G13 |
| Spiro-25 | G2 | G2 | G14 | G14 |
| Spiro-26 | G3 | G3 | G3 | G3 |
| Spiro-27 | G3 | G3 | G4 | G4 |
| Spiro-28 | G3 | G3 | G5 | G5 |
| Spiro-29 | G3 | G3 | G6 | G6 |
| Spiro-30 | G3 | G3 | G7 | G7 |
| Spiro-31 | G3 | G3 | G8 | G8 |
| Spiro-32 | G3 | G3 | G9 | G9 |
| Spiro-33 | G3 | G3 | G10 | G10 |
| Spiro-34 | G3 | G3 | G11 | G11 |
| Spiro-35 | G3 | G3 | G12 | G12 |
| Spiro-36 | G3 | G3 | G13 | G13 |
| Spiro-37 | G3 | G3 | G14 | G14 |
| Spiro-38 | G4 | G4 | G4 | G4 |
| Spiro-39 | G5 | G5 | G5 | G5 |
| Spiro-40 | G6 | G6 | G6 | G6 |
| Spiro-41 | G7 | G7 | G7 | G7 |
| Spiro-42 | G8 | G8 | G8 | G8 |
| Spiro-43 | G9 | G9 | G9 | G9 |
| Spiro-44 | G10 | G10 | G10 | G10 |
| Spiro-45 | G11 | G11 | G11 | G11 |
| Spiro-46 | G12 | G12 | G12 | G12 |
| Spiro-47 | G13 | G13 | G13 | G13 |
| Spiro-48 | G14 | G14 | G14 | G14 |
| Spiro-49 | H | H | G3 | G3 |
| Spiro-50 | H | H | G4 | G4 |
| Spiro-51 | H | H | G5 | G5 |
| Spiro-52 | H | H | G6 | G6 |
| Spiro-53 | H | H | G7 | G7 |
| Spiro-54 | H | H | G8 | G8 |
| Spiro-55 | H | H | G9 | G9 |
| Spiro-56 | H | H | G10 | G10 |
| Spiro-57 | H | H | G11 | G11 |
| Spiro-58 | H | H | G12 | G12 |
| Spiro-59 | H | H | G13 | G13 |

TABLE 1-continued

Spirobi-9-silafluorene derivatives

| Compound | K | L | M | Q |
|---|---|---|---|---|
| Spiro-60 | H | H | G14 | G14 |
| Spiro-61 | G1 | G3 | G3 | G1 |
| Spiro-62 | G1 | G4 | G4 | G1 |
| Spiro-63 | G1 | G5 | G5 | G1 |
| Spiro-64 | G1 | G6 | G6 | G1 |
| Spiro-65 | G1 | G7 | G7 | G1 |
| Spiro-66 | G1 | G8 | G8 | G1 |
| Spiro-67 | G1 | G9 | G9 | G1 |
| Spiro-68 | G1 | G10 | G10 | G1 |
| Spiro-69 | G1 | G11 | G11 | G1 |
| Spiro-70 | G1 | G12 | G12 | G1 |
| Spiro-71 | G1 | G13 | G13 | G1 |
| Spiro-72 | G1 | G14 | G14 | G1 |
| Spiro-73 | G2 | G4 | G4 | G2 |
| Spiro-74 | G2 | G5 | G5 | G2 |
| Spiro-75 | G2 | G6 | G6 | G2 |
| Spiro-76 | G2 | G7 | G7 | G2 |
| Spiro-77 | G2 | G8 | G8 | G2 |
| Spiro-78 | G2 | G9 | G9 | G2 |
| Spiro-79 | G2 | G10 | G10 | G2 |
| Spiro-80 | G2 | G11 | G11 | G2 |
| Spiro-81 | G2 | G12 | G12 | G2 |
| Spiro-82 | G2 | G13 | G13 | G2 |
| Spiro-83 | G2 | G14 | G14 | G2 |
| Spiro-84 | G3 | G4 | G4 | G3 |
| Spiro-85 | G3 | G5 | G5 | G3 |
| Spiro-86 | G3 | G6 | G6 | G3 |
| Spiro-87 | G3 | G7 | G7 | G3 |
| Spiro-88 | G3 | G8 | G8 | G3 |
| Spiro-89 | G3 | G9 | G9 | G3 |
| Spiro-90 | G3 | G10 | G10 | G3 |
| Spiro-91 | G3 | G11 | G11 | G3 |
| Spiro-92 | G3 | G12 | G12 | G3 |
| Spiro-93 | G3 | G13 | G13 | G3 |
| Spiro-94 | G3 | G14 | G14 | G3 |
| Spiro-95 | H | G3 | G3 | H |
| Spiro-96 | H | G4 | G4 | H |
| Spiro-97 | H | G5 | G5 | H |
| Spiro-98 | H | G6 | G6 | H |
| Spiro-99 | H | G7 | G7 | H |
| Spiro-100 | H | G8 | G8 | H |
| Spiro-101 | H | G9 | G9 | H |
| Spiro-102 | H | G10 | G10 | H |
| Spiro-103 | H | G11 | G11 | H |
| Spiro-104 | H | G12 | G12 | H |
| Spiro-105 | H | G13 | G13 | H |
| Spiro-106 | H | G14 | G14 | H |

Some of the hetero-spiro compounds used according to the invention are known and some are new.

The invention accordingly also provides Spiro compound of the formula (IV),

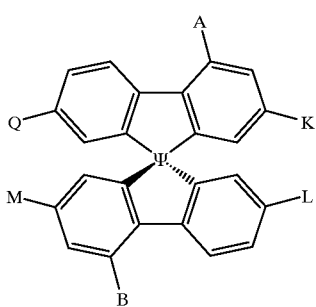

(IV)

where the symbols have the following meanings:

Ψ is Si, Ge or Sn;

A, B, K, L, M, Q are identical or different and are

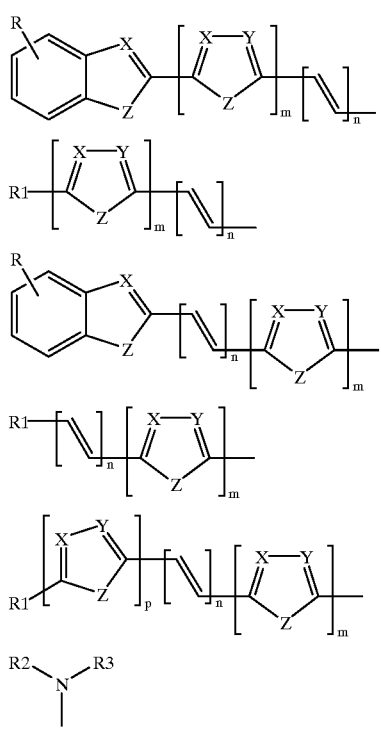

and A, B can also be identical or different and each be a linear or branched alkyl, alkoxy or ester group having from 1 to 22 carbon atoms, —CN, —NO$_2$—Ar or —O—Ar;

R is —H, a linear or branched alkyl, alkoxy or ester group having from 1 to 22, preferably from 1 to 15, particularly preferably from 1 to 12, carbon atoms, —CN, —NO$_2$, —NR$^2$R$^3$, —Ar or —O—Ar;

Ar is phenyl, biphenyl, 1-naphthyl, 2-ndphthyl, 2-thienyl, 2-furanyl, where each of these groups can bear one or two radicals R;

m, n, p are, independently of one another, identical or different and are 0, 1, 2 or 3;

X, Y are identical or different ana are CR, nitrogen;

Z is —O—, —S—, NR$^1$—CR$^1$R$^4$—, —CH=CH—, —CH=N—;

R$^1$, R$^4$ can be identical or different and have the same meanings as R;

R$^2$, R$^3$ are identical or different and are H, a linear or branched alkyl group having from 1 to 22 carbon atoms, —Ar or 3-methylphenyl.

The spiro compounds of the invention or used according to the invention are prepared by literature methods known per se as are described in standard works on organic synthesis, e.g. Houben-Weyl, Methoden der Organischen Chemie, Georg-Thieme-Verlag, Stuttgart, in particular Volume 13/5, pp. 30–87, and in the appropriate volumes of the series "The Chemistry of Heterocyclic Compounds" by A. Weissberger and E. C. Taylor (editors).

The preparation is carried out under reaction conditions which are known and suitable for the reactions specified. Use can here also be made of variants which are known per se and are not mentioned further here. Compounds of the formula (III) are obtained, for example, starting from bis (biphenyl-2,2'-diyl)silane(=9,9'-spirobi(9H-)silafluorene) (V) whose synthesis is described, for example, by H. Gilman, R. D. Gorsich, J. Am. Chem. Soc. 1958, 80, 3243.

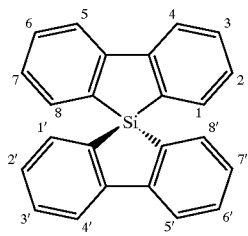

(V)

Compounds of the formula (IIIa) can be prepared, for example, starting with a tetralalgognation in the 2,2',7 and 7' positions of 9,9'-spirobi-9-silafluorene and a subsequent substitution reaction, which are known from analogous C-spiro compounds (see, for example, U.S. Pat. No. 5,026, 894). This can lead, for example via the corresponding cyano compounds, to aldehyde or carbqxylic acid functionality which is used, for example, for building up heterocycles.

Compounds of the formula (IIIb) can be prepared, for example, by methods similar to those for compounds of the formula (IIIa), with the stoichiometric ratios in the reaction being selected such that the 2,2' or 7,7' positions are functionalized (see, for example, J. H. Weisburger, E. K. Weisburger, F. E. Ray, J. Am. Chem. Soc. 1959, 72, 4253; F. K. Sutcliffe, H. M. Shahidi, D. Paterson, J. Soc. Dyers Colour 1978, 94, 306 ana G. Haas, V. Prelog, Helv. Chim. Acta 1969, 52, 1202).

Compounds of the formulae (IIIc) and (IIId) can be prepared, for example, via a dibromination in the 7 and 7' positions of the 2,2'-dicyano-9,9'-spirobi-9-silafluorene, which is synthesized in a manner similar to (IIIa), and subsequent reactions similar to those for compounds (IIIa).

Compounds of the formulae (IIIe)–(IIIg) can be prepared, for example, by selection of suitable substituted starting compounds in building up the spirosilabifluorene, for example:

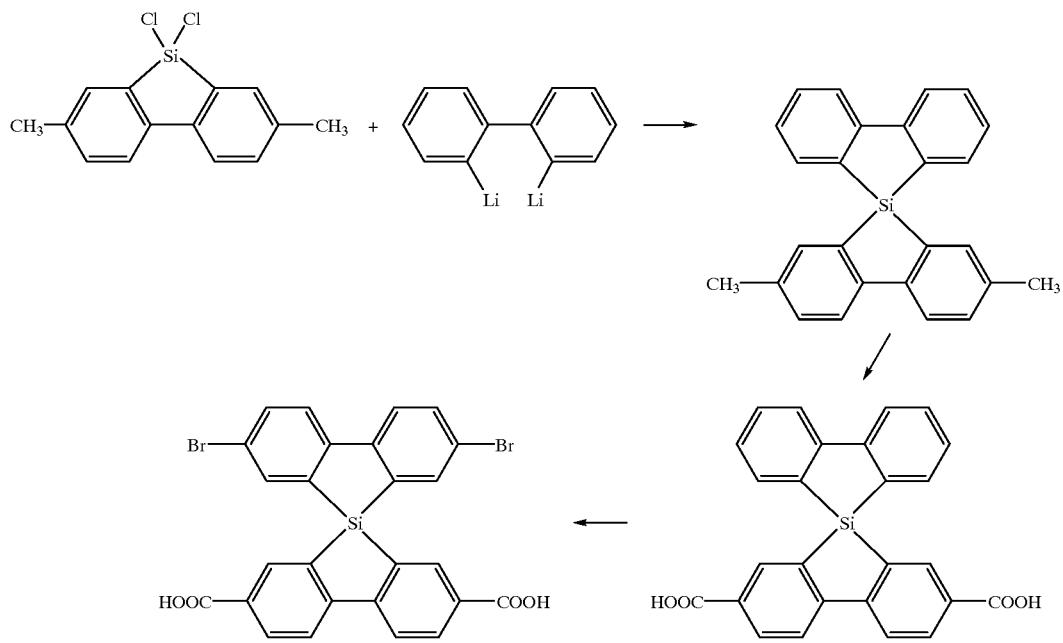

and, for example:

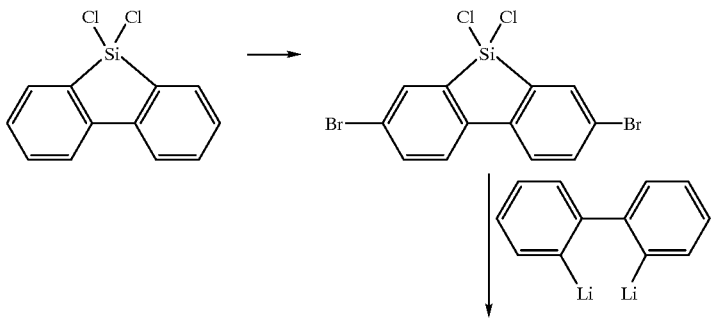

-continued

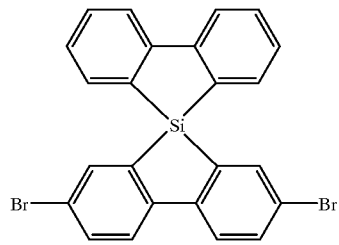

In addition, the synthesis sequences such as nitration, reduction, diazotization and Sandmeyer reaction, with which those skilled in the art are familiar, are to be used. For the synthesis of the groups K, L, M, Q reference may be made, for example, to DE-A 23 44 732, 24 50 088, 24 29 093, 25 02 904, 26 36 684, 27 01 591 and 27 52 975 for compounds containing 1,4-phenylene groups; DE-A 26 41 724 for compounds containing pyrimidine-2,5-diyl grqupri DE-A 40 26 223 and EP-A 0 391 203 for compounds containing pyridine-2,5-diyl groups; DE-A 32 31 462 for compounds containing pyridazine-3,6-diyl groups; N. Miyaura, T. Yanagi and A. Suzuki in Synthetic Communications 11 (1981) 513 to 519, DE-A-39 30 663, M. J. Sharp, W. Cheng, V. Snieckus in Tetrahedron Letters 1987, 28, 5093; G. W. Gray in J. Chem. Soc. Perkin Trans II, 1989, 2041 and Mol. Cryst. Liq. Cryst. 1989, 172, 165, Mol. Cryst. Liq. Cryst. 1991, 204, 43 and 91; EP-A 0 449 015; WO 89/12039; WO 89/03821; EP-A 0 354 434 for the direct linking of aromatics and heteroaromatics.

The preparation of disubstituted pyridines, disubstituted pyrazines, disubstituted pyrimidines and disubstituted pyridazines can be found, for example, in the appropriate volumes of the series "The Chemistry of Heterocyclic Compounds" by A. Weissberger and E. C. Taylor (editors).

According to the invention, the spiro compounds of the formulae (I), (II) and (III) described are used as electroluminescence materials, i.e. they serve as active layer in an electroluminescence device. The invention accordingly also provides an electroluminescence material comprising one or more compounds of the formulae (I), (II) and/or (III). For the purposes of the invention, active layers are electroluminescence materials which are 30 capable of emitting light on application of an electric field (light-emitting layer), and also materials which improve the injection and/or the transport of the positive and/or negative charges (charge injection layers and charge transport layers).

The invention accordingly also provides an electroluminescence device having one or more active layers comprising one or more compounds of the formulae (I), (II) and/or (III). The active layer can be, for example, a light-emitting layer and/or a transport layer and/or a charge injection layer. Emphasis should be given to the excellent hole-conducting properties of the materials of the invention, which can be used as d hole transport layer in, for example, photocopiers and laser printers. The general structure of such electroluminescence devices is described, for example, in U.S. Pat No. 4,539,507 and U.S. Pat No. 5,151,629.

They usually comprise an electroluminescing layer between a cathode and an anode, with at least one of the electrodes being transparent. In addition, an electron injection and/or electron transport layer can be introduced between the electroluminescing layer and the cathode and/or a hole injection and/or hole transport layer can be introduced between the electroluminescing layer and the anode. Suitable cathodes are, for example, Ca, Mg, Al, In, Mg/Ag.

Suitable anodes are, for example, Au or ITO (indium oxide/tin oxide on a transparent substrate, e.g. of glass or a transparent polymer).

In operation, the cathode is placed at a negative potential compared with the anode, and electrodes from the cathode are thus injected into the electron injection layer/electron transport layer or directly into the light-emitting layer. At the same time, holes from the anode are injected into the hole injection layer/hole transport layer or directly into the light-emitting layer.

The injected charge carriers move towards one another through the active layers under the action of the applied potential. This leads, at the interface between charge transport layer and light-emitting layer or within the light-emitting layer, to electron/hole pairs which recombine with emission of light.

The color of the emitted light can be varied by means of the compound used as light-emitting layer, with express reference also being made to mixtures of the materials of the invention with one another and also with other materials, e.g. corresponding carbo-spiro compounds.

Electroluminescence devices are used, for example, as self-illuminating display elements such as control lamps, alphanumeric displays, signs, and in optoelectronic couplers.

The invention is illustrated by the examples without being restricted thereto.

EXAMPLES

Example 1

2,2'-Dilithiobiphenyl 26 ml of a solution of 28 mmol of n-BuLi in absolute diethyl ether (ether) were added dropwise over a period of 5 minutes to an ice-cooled, vigorously stirred solution of 4.0 g (12.9 mmol) of 2,2'-dibromobiphenyl in 40 ml of ether and the mixture was subsequently stirred for 5 hours at room temperature.

Example 2

Bis(biphenyl-2,2'-diyl)silane (9,9'-spirobi-9-silafluorene)

A solution of 24 mmol of 2,2'-dilithiobiphenyl in 70 ml of ether prepared as described in Example 1 was added dropwise over a period of one hour to a vigorously stirred solution of 1.87 g (11 mmol) of silicon tetrachloride in 30 ml of ether. The mixture was stirred for a further 1.5 hours at room temperature and was refluxed for 3 hours. 50 ml of benzene were subsequently added and the mixture was refluxed for a further 2 hours. After shaking with 100 ml of water, the organic phase is dried over magnesium sulfate and filtered, the major part of the ether was distilled off on a rotary evaporator. From the cooled solution, 1.45 g of crude product laving a melting point of from 222 to 225° C. were isolated. After evaporation, the filtrate gave a further 0.6 g of product (total yield 56%). Crystallization from ethanol gave a melting point of 227° C. Elemental analysis:

| %     | C     | H    | Si   |
|-------|-------|------|------|
| calc. | 86.72 | 4.85 | 8.44 |
| found | 86.86 | 4.98 | 8.33 |

The remarkably high stability of this compound is shown by the boiling point of 460° C., which is reached without visible decomposition.

Example 3

Bis(biphenyl-2,2'-diyl)germane (9,9'-spirobi-9-germafluorene)

A solution of 50 mmol of 2,2'-dilithiobiphenyl prepared in 140 ml of ether, as described in Example 1, was reacted as described in Example 2 with 5.35 g (25 mmol) of germanium tetrachloride. After work-up and recrystallization from ethyl acetate, 2.77 g (29%) of product were obtained. White prisms, melting point 245° C., boiling point 470° C. without decomposition. Elemental analysis:

| %     | Ge    |
|-------|-------|
| calc. | 19.23 |
| found | 18.88 |

Example 4

Biphenyl-2,2'-diylsilicon dichloride 78 mmol of 2,2'-dilithiobiphenyl prepared in 230 ml of ether, as described in Example 1, were reacted as described in Example 2 with 252 g (1.48 mol, i.e. 18-fold excess) of silicon tetrachloride. After distilling off the excess $SiCl_4$ and working-up, 3.5 g of a solid product were obtained and after recrystallization from ethyl acetate this gave 2.89 g (22 %) of bis(biphenyl-2,2'-diyl) silane as described in Example 2. The combined mother liquors were evaporated and the remaining oil was distilled at 0.01 mbar, with a small amount of biphenyl going over as initial fraction and 7.41 g (38%) of biphenyl-2,2'-diylsilicon dichloride going over as main fraction at from 108 to 110° C.

| %     | Cl   | Si    |
|-------|------|-------|
| calc. | 28.3 | 11.33 |
| found | 26.5 | 10.75 |

Example 5

10,10-Biphenyl-2,2'-diylphenoxasilin

A solution of 120 mmol of 2,2'-dilithiodiphenyl ether in 180 ml of THF, prepared as described by H. Gilman, W. J. Trepka, J. Org. Chem. 27, 1418 (1962), was added to a solution of 37.7 g (150 mmol) of biphenyl-2,2'-diylsilicon dichloride in 200 ml of THF, prepared as described in Example 4. The mixture was stirred for 12 hours at 20° C., hydrolyzed using a mixture of ice and sulfuric acid and the aqueous phase was extracted with ether. After distillating work-up at $\leq 0.05$ mm, the main fraction going over at 150° C. was recrystallized from ethanol: 12.5 g (30%).

Example 6

Bis(bibenzyl-2,2'-diyl)silane

A solution of 2.1 ml (20 mmol) of silicon tetrachloride in 50 ml of THF was added dropwise to a solution of 2,2'-dilithiobibenzyl which had previously been prepared from 15 g (40 uirol) of 2,2'-dibromobibenzyl and 97 mmol of a 1.7 molar solution of n-butyllithium in a hexane fraction. The mixture was refluxed for 1 hour and worked-up as in Example 5. 5.0 g of a solidifying oil went over at a pressure of 0.05 mm between 125 and 210° C., and after being recrystallized twice this gave 1.0 g (12%) of bis(bibenzyl-2,2'-diyl)silane having a melting point of 175° C. Elemental analysis:

| %     | C     | H    |
|-------|-------|------|
| calc. | 86.60 | 6.19 |
| found | 86.21 | 6.05 |

Example 7

Bis(stilbene-2,2'-diyl)silane from bis($\alpha,\alpha'(\beta')$-dibromobibenzyl-2,2'-diyl)silane A slurry of 1.94 g (5 mmol) of bis(bibenzyl-2,2'-diyl) silane, prepared as described in Example 6, and 1.78 g (10 mmol) of N-bromosuccinimide in 100 ml of tetrachloromethane were heated to boiling under irradiation with a 300 W incandescent tungsten lamp. The succinimide formed was filtered off with suction, the filtrate was evaporated to dryness on a rotary evaporator, the residue was taken up in 15 ml of toluene and admixed with 2 ml of 2-dimethylaminoethanol. The mixture was stirred for 48 hours and then heated to boiling for 6 hours. The toluene was removed in vacuo, the residue was admixed with 50 ml of 5% strength by weight sodium hydroxide solution and shaken with ether. After drying over magnesium sulfate, the ether was evaporated and the residue was purified by chromatography in toluene/cyclohexane on 30 g of silica gel.

Example 8

3,3',5,5'-Tetraphenyl-9,9'-spiro-9H-bi-9-silafluorene from tetrakis(biphenylyl-4)silane 10.8 g (46.3 mmol) of 4-bromobiphenyl together with 1.95 g (11.6 mol) of silicon tetrachloride were dissolved in 100 ml of absolute ether and subsequently treated with 2.5 g (110 mmol) of sodium. The mixture was heated to reflux and then stirred for a further 4 hours at room temperature until the metal had dissolved. After removal of the ether, the residue was extracted with toluene in a Soxhlet apparatus: 6.7 g (90%), mp. 281° C. from xylene.

5.4 g (10 mmol) of tetrakis(biphenylyl-4)silane were dissolved in 200 ml of 1,2-dichlorobenzene and, while passing nitrogen through the solution, was admixed in portions with 6.5 g (40 mmol) of iron(III) chloride. The mixture was heated to boiling over a period of 3 hours.

When HCl could no longer be detected as NH$_4$Cl in the off-gas, the mixture was evaporated on a rotary evaporator, the residue was digested a number of times with 5% strength by weight hydrochloric acid and the residue was recrystallized from xylene with addition of 1 g of silica gel: 2.7 g (51%).

Example 9

2,2'-Dinitro-9,9'-spiro-9-silabifluorene 3.16 g (13 mmol) of Cu(NO$_3$)$_2$.3 H$_2$O are taken up at room temperature using 20 ml of acetic anhydride and stirred. After a few minutes, the internal temperature rises to about 40–45° C. with the blue suspension becoming turbid. 2 g (6 mmol) of 9-sila-9,9'-spirobifluorene are subsequently added and stirring is continued at 40° C. After 4 hours at 40° C., the reaction is complete. During the reaction, the color of the suspension changed to turquoise. It is carefully stirred into about 100 ml of water and shaken with chloroform. After evaporating the organic phase on a rotary evaporator and dialoguing the residue in a little chloroform, the solution is precipitated with 100 ml of hexane: 2 g of colorless product (79%).

2,2',7,7'-Tetranitro-9,9'-spiro-9-silabifluorene can be obtained as main product by a similar route using a different stoichiometry.

Example 10

2,2'-Diamino-9,9'-spiro-9-silabifluorene

A mixture of 4.0 g of dinitrospiro-9-silabifluorene and 4.0 g of iron powder were refluxed in 100 ml of ethanol while 15 ml of concentrated hydrochloric acid were added dropwise over a period of 30 minutes. After refluxing for a further 30 minutes, excess iron was filtered off. The green filtrate was added to a solution of 400 ml of water, 15 ml of concentrated NH$_4$OH solution and 20 g of sodium potassium tartrate. The white diamine was filtered off from the dark green solution of the iron complex. The diamine was purified by dissolving it in dilute hydrochloric acid, stirring at room temperature with activated carbon (Darco) and filtration. The filtered solution was neutralized dropwise with NH$_4$OH solution while stirring mechanically (precision glass stirrer) and the precipitated product was filtered off with suction. This gave 3.3 g of white 2,2'-diamino-9,9'-spiro-9-silabifluorene which was recrystallized from ethanol.

2,2',7,7'-Tetraamino-9,9'-spiro-9-silabifluorene can be obtained as main product by a similar method using a different stoichiometry.

Example 11

2,2'-Dibromo-9,9'-spiro-9-silabifluorene 2.0 g (5.5 mmol) of 2,2'-diamino-9,9'-spiro-9-silabifluorene are dissolved in 20 ml of water and 5 ml of concentrated hydrobromic acid, cooled to about 0° C. and slowly admixed with a solution of 0.8 g of NaNO$_2$ in about 5 ml of water while maintaining this temperature. The mixture is stirred at this temperature for about 30 mins, and the solution of the resulting bisdiazonium salt is poured into an ice-cooled solution of 1 g of CuBr in 10 ml of HBr. The resulting solution is stirred at 100° C., with gas evolution occurring and the product formed being precipitated as a white deposit. After gas evolution has ended, the product is filtered off with suction, washed with NaRCO$_3$ solution until neutral and washed with water until free of salts. The product is subsequently reprecipitated from chloroform/hexane: 1.8 g of colorless powder (66%).

2,2',7,71-Tetrabromo-9,9'-gpiro-9-silabifluorene can be obtained as main product from 2,2',7,7'-tetraamino-9, 9'spiro-9-silabifluorene by a similar route using a different stoichiometry.

Example 12

9,9'-Spiro-9-silabifluorene-2,2'-dicarboxylic acid from 2,2'-dibromo-9,9'-spiro-9-silabifluorene via 2, 2'-dicyano-9,9'-spiro-9-silabifluorene 1.18 g (2.4 mmol) of 2,2'-dibromo-9,9'-spiro-9-silabifluorene, as described in Example 11, and 0.54 g of CuCN were refluxed for 6 hours in 5 ml of DMF. The brown mixture obtained was poured into a mixture of 3 g of FeCl$_3$ (hydrated) and 1.5 ml of concentrated hydrochloric acid in 20 ml of water. The mixture was maintained at from 60 to 70° C. for 30 minutes to destroy the Cu complex.

The hot aqueous solution was extracted twice with toluene. The organic phases were then washed with dilute hydrochloric acid, water and 10% strength by weight aqueous NaOH. The organic phase was filtered and evaporated. The yellow residue obtained was recrystallized from methanol. This gave 0.64 g (70%) of 2,2'-dicyano-9,9'-spiro-9-silabifluorene as slightly yellowish crystals (melting range from 230 to 260° C.).

3.82 g (10 mmol) of 2,2'-dicyano-9,9'-spiro-9-silabifluorene were refluxed for 6 hours with 30 ml of 30% strength by weight NaOH and 40 ml of ethanol. The disodium salt of the spirosilabifluorenedicarboxylic acid precipitated as a yellow solid which was filtered off and heated in 25% strength by weight aqueous HCl to isolate the free acid. The spirosilabifluorenedicarboxylic acid was recrystallized from glacial acetic acid. This gave 2.52 g (60%) of white crystals (mp. >360° C., IR band at 1685 cm$^{-1}$, C=O).

Example 13

9,9'-Spiro-9-silabifluorene-2,2',7,7'-tetracarboxylic acid was prepared in a similar manner from 2,2',7,7'-tetrabromo-9,9'-spiro-9-silabifluorene.

Example 14

2,2'-Bis(bromomethyl)-9,9'-spiro-9-silabifluorene from 9,9'-spiro-9-silabifluorene 2,2'-dicarboxylic acid via 2,2'-bis (hydroxymethyl)-9,9'-spiro-9-silabifluorene using a method similar to that of V. Prelog, D. Bedekovicc, Helv. Chim. Acta 1979, 62, 2285

At room temperature, 10 g of a 70% strength by weight solution of sodium dihydrobis (2-methoxyethoxy) aluminate (Fluka) in toluene were slowly added dropwise to a suspension of 2.08 g (5 mmol) of 2,2'-dicarboxy-9,9'- spiro-9-silabifluorene-2,2'-dicarboxylic acid in 20 ml of toluene. After refluxing for 2 hours, during which time the carboxylic acid dissolved, the excess reducing agent was decomposed at 10° C. using water, the mixture was acidified with concentrated hydrochloric acid and shaken with chloroform.

The organic phase which had been washed with water and dried over magnesium sulfate was evaporated and the residue was recrystallized from benzene. This gave 1.7 g of 9,9'-spiro-9-silabifluorene-2,2'-dimethanol (mp.>250° C.). 92 g of a 33% strength by weight aqueous solution of hydrogen bromide in glacial acetic acid were added dropwise to a solution of 14 g of 9,9'-spiro-9-silabifluorene-2, 2'-dimethanol in 400 ml of toluene and the mixture was refluxed for 7 hours. It was then admixed with 200 ml of water and the organic phase was washed with water, dried over magnesium sulfate and evaporated. Chromatography on silica gel using toluene gives 11 g of 2,2'-bis (bromomethyl)-9,9'-spiro-9-silabifluorene as colorless platelets.

Example 15

A solution of 0.4 g of 9,9'-spiro-9-silabifluorene-2,2'-dimethanol, as described in Example 14, in 15 ml of toluene was admixed with 5 g of chromium(VI) oxide on graphite (Seloxcette, Alpha Inorganics) and refluxed for 48 hours under nitrogen. The mixture was then filtered with suction through a sintered glass filter and the filtrate was evaporated. Chromatography on silica gel using chloroform and crystallization from methylene chloride/ether gave 150 mg of 9,9'-spiro-9-silabifluorene-2,2'-dicarbaldehyde (mp.>300° C.) and 200 mg of 2'-hydroxymethyl-9,9'-spiro-9-silabifluorene-2-carbaldehyde (mp.>260° C.).

Example 16

2,2'-Bis(benzofuran-2-yl)-9,9'-spiro-9-silabifluorene using a method similar to that of W. Sahm, E. Schinzel, P. Jürges, Liebigs Ann. Chem. 1974, 523.

2.7 g (22 mmol) of salicylaldehyde and 5.4 g (10 mmol) of 2,2'-bis(bromomethyl)-9,9'-spiro-9-silabifluorene, as described in Example 14, were dissolved at room temperature in 15 ml of DMF and admixed with 0.9 g (22.5 mmol) of pulverized NaOH and a spatula tip of KI. The mixture was heated to boiling and stirred for 1 hour at the boiling temperature. After cooling, the reaction solution was admixed with a mixture of 0.5 ml of concentrated hydrochloric acid, 7 ml of water and 7 ml of methanol. Stirring was continued for 1 hour at room temperature, the crystalline reaction product was filtered off with suction, washed first with cold methanol, then with water and dried in vacuo at 60° C. This gave 4.6 g (79%) of the bigbenzylphenyl ether. 6.0 g (10 mmol) of the bisbenzylphenyl ether were admixed in 10 ml of toluene with 2.1 g (22.5 mmol) of freshly distilled aniline. A spatula tip of p-toluenesulfonic acid was added and the mixture was boiled attached to a water separator until water no longer separated (from about 3 to 5 hours). On cooling the reaction mixture, the corresponding bisbenzylidenephenylamine crystallized. It was filtered off with suction, washed with methanol and dried in vacuo at 60° C. It can be further purified by recrystallization from DMF. 7.5 g (10 mmol) of the bisbenzylidenaphenylamine and 0.62 9 (11 mmol) of KOH are introduced under nitrogen into 30 ml of DMF. The mixture is subsequently heated at 100° C. for 4 hours while stirring. After cooling to room temperature, the precipitate was filtered off and washed with a little DMF and water. After drying at 600C in a vacuum drying oven, the 2,2'-bis (benzofuran-2-yl) -9,9'-spiro-9-silabifluorene was purified by recrystallization from methyl benzoate.

Example 17

2,2',7,7'-Tetrakis(benzofuran-2-yl)-9,9'-spiro-9-silabifluorere was prepared using a method similar to Example 1 with an appropriately changed stoichiometry.

Example 18

2,2',7,7'-Tetraphenyl-9,9'-spiro-9-silabifluorene 5.1 g (7.9 mmol) of 2,2',7,7'-tetrabromo-9,9'-spiro-9-silabifluorere 3.86 g (31.6 mmol) of phenylboronic acid, 331.5 mg (1.264 mmol) of triphenyiphosphine and 70.9 mg (O.316 minol) of palladium acetate were slurried in a mixture of 65 ml of toluene and 40 ml of aqueous sodium carbonate solution (2M). The mixture was refluxed for 24 hours while stirring vigorously. After cooling to room temperature, it was filtered with suction, the solid washed with water and dried at 50° C. in vacuo. This gave 2.4 g of product. The filtrate was extracted with 50 ml of toluene and the dried organic phase was evaporated to dryness. This gave a further 1.42 g of product. Total yield: 3.82 g (76%)

Example 19

2,2',7,7'-Tetrakis(biphenyl-4-yl)-9,9'-spiro-9-silabifluorene 5.1 g (7.9 mool) of 2,2',7,7'-Tetrabromospiro-9-silabifluorene, 6.57 g (33.2 mmol) Of biphanylylboronic acid, 331.5 mg (1.264 mmcol) of triphenylphosphine and 70.9 mg (0.316 mmol) of palladium acetate were slurried in a mixture of 65 ml of toluene and 40 ml of aqueous sodium carbonate solution (2M). The mixture was refluxed for 24 hours while stirring vigorously. After cooling to room temperature, it was filtered with suction, the solid was washed with water and dried at 50° C. in vacuo. Yield: 5.87 g (79%).

Example 20

Synthesis of 2,2',7,7'-tetrakis(biphenyl-4-yl)-9,9'-spiro-9-silabifluorene

In a 250 ml two-neck flask fitted with reflux condenser and precision glass stirrer, 5.5 g of 2,2',7,7'-tetrabromospiro-9-silabifluorene, 7.2 g of 4-biphenylylboronic acid and 400 mg of tetrakis(triphenylphosphine)palladium(0) were slurried in a mixture of 100 ml of toluene and 50 ml of potassium carbonate solution. The mixture was refluxed for 8 hours under a blanket of protective gas while stirring with a precision glass stirrer. After cooling, the product was filtered off with suction, the precipitate was washed with water and dried. In the filtrate, the toluene phase was separated off and the aqueous phase was shaken once with chloroform. The combined organic phases were dried over sodium sulfate and evaporated, thus giving a second fractional of the product. The two product fractions were combined (8 g) and dissolved in chloroform. The chloroform solution was boiled with activated carbon and filtered through a short column containing silica gel. Evaporation and recrystallization from chloroform/pentane gave colorless crystals which fluoresced blue under UV illumination. Melting point: 408° C. (DSC).

$^1$H-NMR (CDC$_3$, ppm): 7.14 (d, J=1.53 Hz, 4 H); 7.75 (dd, J=7.93, 1.53 Hz, 4 H); 8.01 (d, J=7.93 Hz, 4 H); 7.34 (dd, J=7.32, 1.37 Hz, 4 H); 7.42 (t, J=7.32 Hz, 8 H); 7.Sf (24 H).

Example 21

Synthesis of 2,2'-bis[(5(p-t-butylphenyl)-1,3,4-oxadiazol-2-yl]9,9'-spiro-9-silabifluorene from 9,9'-spiro-9-silabifluorene-2,2'-dicarboxylic chloride and 5-(4-butylphenyl)tetrazole 21a) Synthesis of 5-(4-t-butylphenyl)tetrazole In a 250 ml round-bottom flask fitted with reflux condenser, 4.9 g of p-t-butylbenzonitrile, 3.82 g of lithium chloride and 5.85 g of sodium azide and 8.2 g of triethylammonium bromide in 100 ml of DMF were heated at 120° C. for 8 hours. After cooling to room temperature, 100 ml of water were added and the mixture was admixed in an ice bath with dilute hydrochloric acid until no further precipitate was formed. The mixture was filtered with suction, the precipitate was washed with water and dried. Recrystallization from ethanol/water gave 4.4 g of colorless crystals.

21b) 9,9'-Spiro-9-silabifluorene-2,2'-dicarboxylic chloride

In a 100 ml round-bottom flask fitted with reflux condenser and drying tube, 2.1 g (5 mmol) of 9,9'-spiro-9-silabifluorene-2,2'-dicarboxylic acid, as described in Example 12, were refluxed for 4 hours with 20 ml of (freshly distilled) thionyl chloride and 3 drops of DMF. After cooling, the reflux condenser was replaced by a distillation bridge and excess thionyl chloride was distilled off in vacuo. 40 ml of petroleum ether (boiling point: 30°–60° C.) were added to the residue and distilled off, leaving the crystalline acid chloride.

21c) 2,2'-Bis[(5-(p-t-butylphenyl)-1,3,4-oxadiazol-2yl]9,9'-spiro-9-silabifluorene 2.0 g (11 mmol) of 5-(4-t-butylphenyl)tetrazol dissolved in 20 ml of anhydrous pyridine were added as described in Example 21.b to the acid chloride and the mixture was refluxed for 2 hours under protective gas. After cooling, the mixture was poured into 200 ml of water and allowed to stand for 2 hours. The precipitated oxidiazole derivative was filtered off with suction, washed with water and dried in vacuo. It was subsequently chromatographed on silica gel using chloroform/ethyl acetate (99:1) and recrystallized from chloroform/pentane. This gave 2.3 g of colorless crystals.

Example 22

2,2',7,7'-Tetrakis(biphenyl)-4-yl)-9,9'-spiro-9-silabifluorene, as described in Example 19, was dissolved in chloroform (30 mg/ml) and applied by means of spin coating (1,000 rpm) to a glass support coated with 30 indium/tin oxide (ITO), with a homogeneous, transparent film being formed. An electrode of Mg/Ag (80/20) was applied to this film by vacuum deposition. On application of an electric potential between the ITO electrode and the metal electrode, with the metal electrode having a negative potential compared with the ITO electrode, a blue electroluminescence was observed.

Example 23

As described in Example 22, further test specimens were produced by vacuum deposition onto an ITO layer (30 Ohm), with the following parameters being obtained:

thickness of the 2,2',7,7'-tetrakis(biphenyl-4-yl)-9,9'-spiro-9-silabifluorene layer $a_1$=60 nm, thickness of the aluminum tris(8-oxyquinoline) layer: $b_1$=20 nm, thickness of the Al+Mg (3%) layer: $c_1$=135 nm, analogous test specimen: $a_2$=60 nm, $b_2$=0 nm, $a_3$=41 nm, $b_3$=150 nm.

All three test specimens showed blue electroluminescence.

What is claimed is:

1. A hetero-spiro compound of the formula

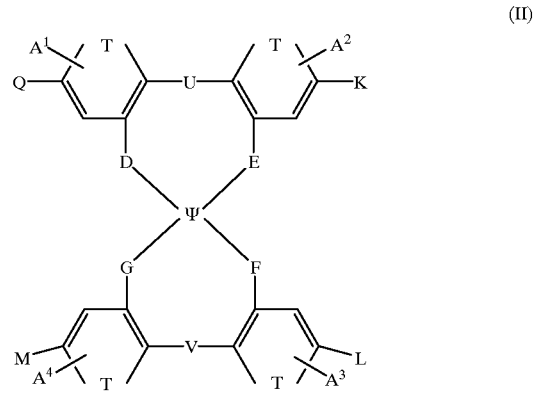

(II)

wherein

Ψ is Si, Ge, Sn;

D, E, F, G are identical or different and are —CR$^1$R$^2$—, —O—, —S—, —NR$^3$— or a chemical bond;

U, V are identical or different and are —CR$^1$R$^2$—, —O—, —S—, NR$^3$—, —SiR$^1$R$^2$—, —SO$_2$—, —CO—, —CR$^4$=CR$^5$— or a chemical bond, with the proviso that at least one of U or V is —CR$^1$=CR$^2$— or a chemical bond;

T is —O—, —S—, —NR$^3$—, —CR$^1$R$^2$—, —CH=N—, —CA$^5$=CA$^6$—, —CH=CA$^7$—;

K, L, M, Q are identical or different, cyclic or acyclic hydrocarbon radicals which have conjugated electron systems and can also contain heteroatoms;

A$^1$, A$^2$, A$^3$, A$^4$, are identical or different and have the same meaning as K, L, M, Q or are hydrogen, fluorine, a hydrocarbon radical having from 1 to 22 carbon atoms which can also contain heteroatoms, —CN, —NO$_2$, or —NR$^6$'R$^7$'

A$^6$ is hydrogen

A$^5$ and A$^7$ are identical or different and are

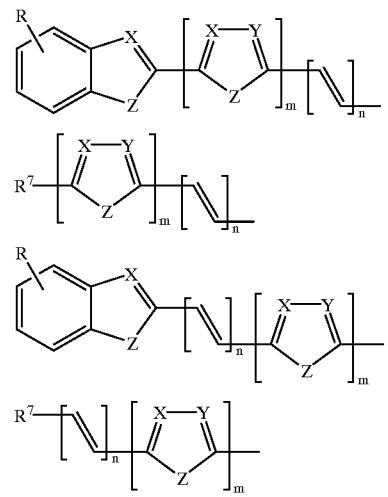

-continued

[structure with X, Y, Z, R7, R8, R9, N, p, n, m indices]

or are identical or different and are a linear or branched alkyl, alkoxy or ester group having from 1 to 22 carbon atoms, —CN, —NO$_2$, —Ar or —O—Ar;

R is —H, a linear or branched alkyl, alkoxy or ester group having from 1 to 22 carbon atoms, —CN, —NO$_2$, —NR$^9$'R$^{10}$', —Ar or —O—Ar;

Ar is phenyl, biphenyl, 1-naphthyl, 2-naphthyl, 2-thienyl, 2-furanyl, where each of these groups can bear one or two radicals R;

m, n, p are, independently of one another, identical or different and are 0,1,2, or 3;

X, y are identical or different and are CR, nitrogen;

Z is —O—, —S—, —NR$^7$—, —CR$^7$R$^{10}$—, —CH=CH—, —CH=N—;

R$^7$, R$^{10}$ can be identical or different and have the same meanings as R;

R$^8$, R$^9$ are identical or different and are H, a linear or branched alkyl group having from 1 to 22 carbon atoms, —Ar or 3-methyiphenyl R$^9$', R$^{10}$' are identical or different and are H, a linear or branched alkyl group having from 1 to 22 carbon atoms, —Ar, or 3-methylphenyl, R$^1$, R$^2$, R$^3$ are identical or different and are H or a hydrocarbon radical having from 1 to 12 carbon atoms, where R$^1$ and R$^2$ can together also form an unsubstituted or substituted ring;

R$^4$, R$^5$ are identical or different and have the same meanings as R$^1$, R$^2$, R$^3$ or are fluorine or —CF$_3$;

R$^{6'}$, R$^{7'}$ are identical or different and are H or a hydrocarbon radical having from 1 to 22 carbon atoms which can be aliphatic or aromatic, linear or branched and can also contain alicyclic elements, or R$^{6'}$ and R$^{7'}$ together form a ring;

Q and A$^1$, K and A$^2$, L and A$^3$, M and A$^4$ can also each be joined together to form a ring which can be saturated, partially unsaturated or having maximum unsaturation.

2. A hetero-spiro compound according to claim 1, wherein Ψ is Ge or Sn.

3. An electroluminescence material which comprises one or more hetero-spiro compounds according to claim 1.

4. An electroluminescence device comprising a cathode, one or more active layers and an anode, wherein at least one of these active layers comprises an electroluminescence material according to claim 3.

5. The electroluminescence device according to claim 4, wherein the active layer comprising the electroluminescence material is a light-emitting layer.

6. The electroluminescence device according to claim 4, wherein the active layer comprising the electroluminescence material is a transport layer.

7. The electroluminescence device according to claim 4, wherein the active layer comprising the electroluminescence material is a charge injection layer.

8. A hetero-spiro compound according to claim 1, wherein

Ψ is Si;

D, E, F, G are a chemical bond;

U and V are a direct bond;

T is —CH=CH—;

K, L, M, Q are biphenyl;

A$^1$, A$^2$, A$^3$, A$^4$ are identical or different and have the same meanings as K, L, M, Q or are hydrogen, fluorine, or a hydrocarbon radical having from 1 to 22 carbon atoms.

9. The hetero-spiro compound according to claim 8, which has the following structure:

[structure: spiro-Si compound with biphenyl groups]

10. A hetero-spiro compound, which has the formula:

(III)

[structure with Q, K, M, L, A, Ψ]

wherein

ω is Si or Ge;

K, L, M, Q, A are identical or different and are

[structure with R, X, Y, Z, m, n]

-continued

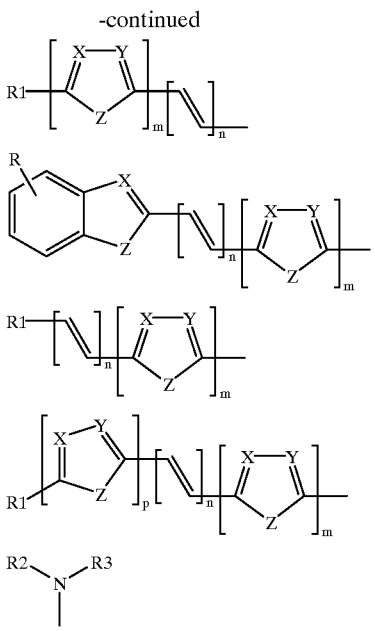

and, in addition, K, L, M, Q may also be identical or different and be

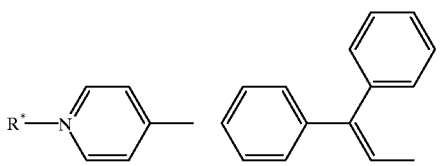

wherein

R* is $C_1$–$C_{22}$-alkyl or —$(CH_2)_x$—$SO_3^-$, where x is 2, 3 or 4 and A may also be identical or different and be linear or branched alkyl, alkoxy or ester group having from 1 to 22 carbon atoms, —CN, —$NO_2$, —$NR^2R^3$, —Ar or —OAr;

R is identical or different and has the same meanings as K, L, M, Q or is —H, a linear or branched alkyl, alkoxy or ester group having from 1 to 22 carbon atoms, —CN, —$NO_2$, —$NR^2R^3$, —Ar or —O—Ar;

Ar is phenyl, biphenyl, 1-naphthyl, 2-naphthyl, 2-thienyl, 2-furanyl, where each of these groups are optionally substituted by one or two radicals R, m, n, p are, independently of one another, identical or different and are 0, 1, 2 or 3;

X, Y are identical or different and are CR, N;

Z is —O—, —S—, —$NR^1$—, —$CR^1R^4$—, —CH=CH—, —CH=N—;

$R^1$ has the same meanings as R;

$R^4$ has the same meaning as R, $R^2$, $R^3$ are identical or different and are H, a linear or branched alkyl group having from 1 to 22 carbon atoms, —Ar, or 3-methylphenyl.

11. The hetero-spiro compound according to claim 10, wherein the hetero-spiro compound is heterospirobifluorene derivative selected from the group consisting of IIIa) K=L=M=Q and are selected from the group consisting of:

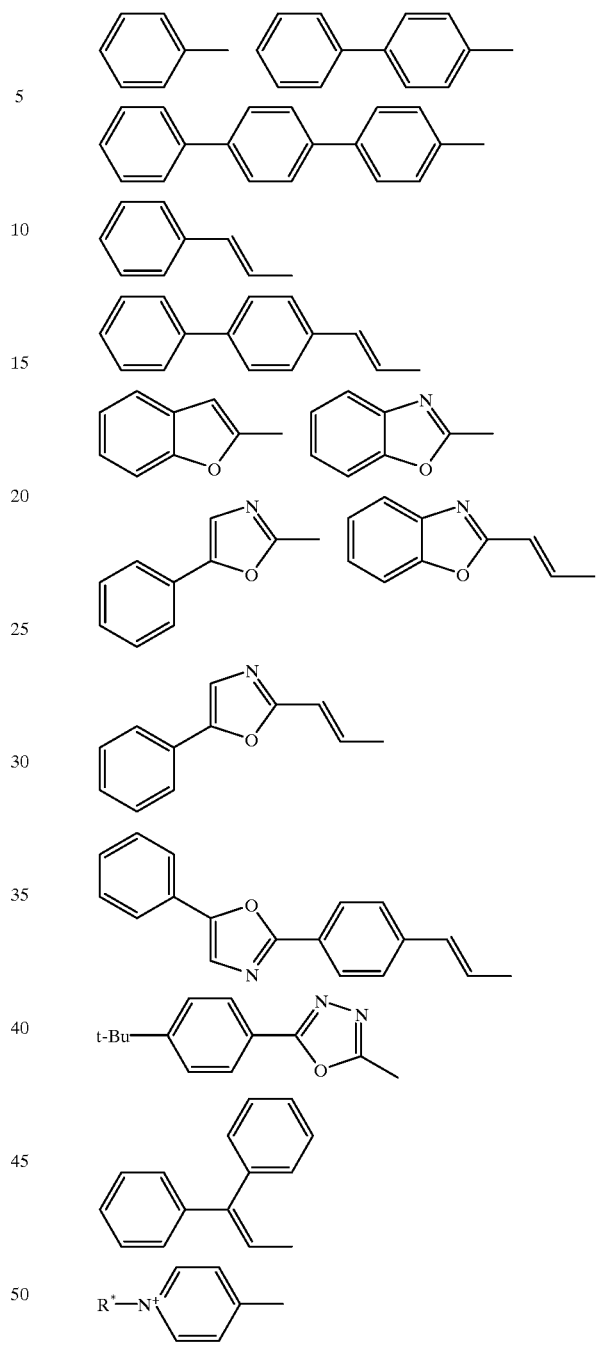

R*=$C_1$–$C_{22}$-alkyl, or —$(CH_2)_x$—$SO_3^-$ where x=2,3 or 4

IIIb) K=M=H and Q=L and are selected from the group consisting of:

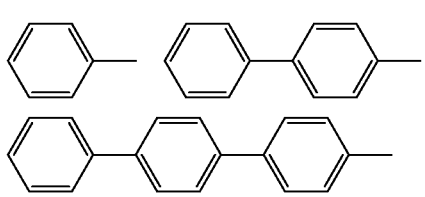

-continued
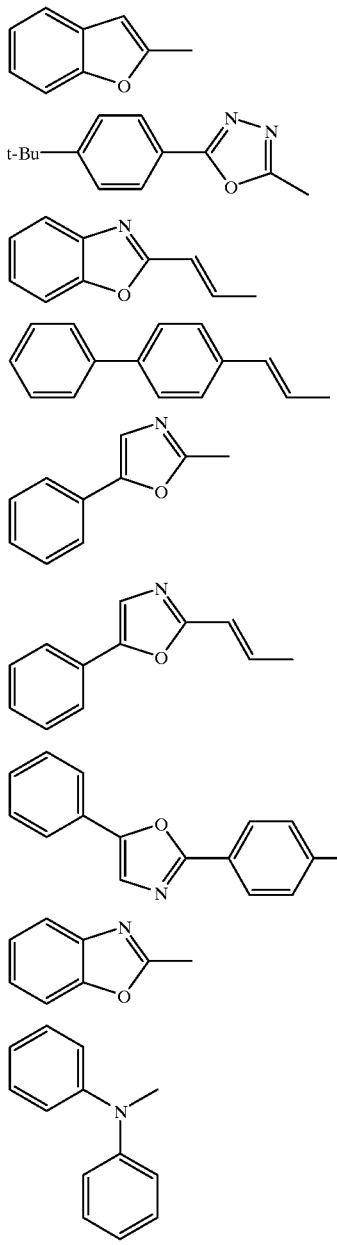
IIIc) K=M and are selected from the group consisting of:
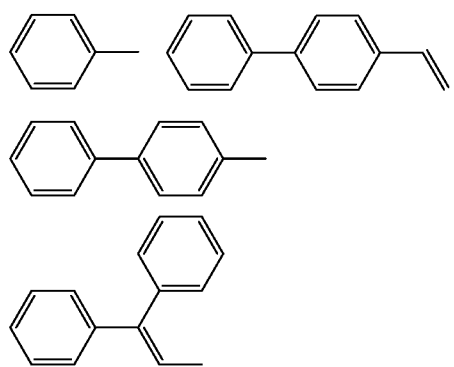
-continued
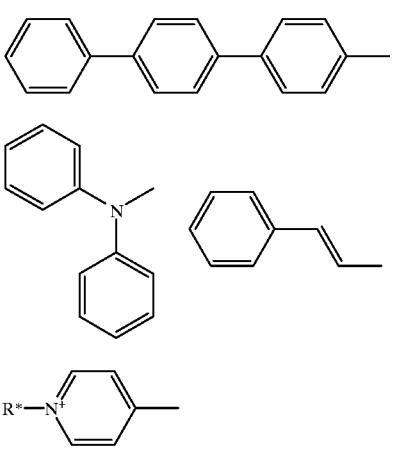
$R^* = C_1-C_{22}$-alkyl, or $-(CH_2)_x-SO_3^-$ where x=2,3 or 4 and
Q=L and are selected from the group consisting of:
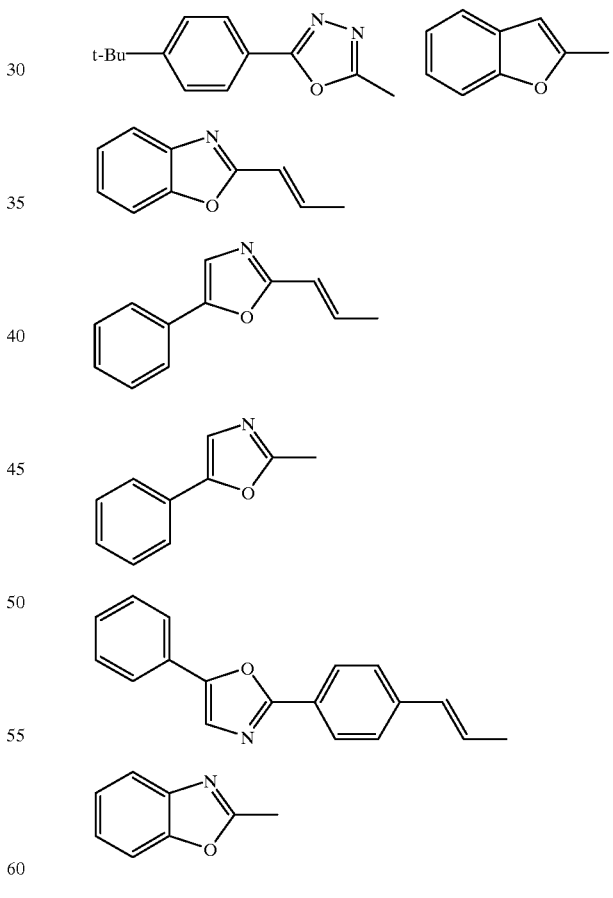

IIId) K=M and are selected from the group consisting of:

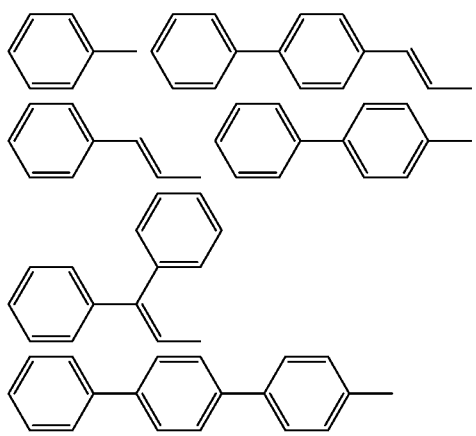

and Q=L and are selected from the group consisting of:

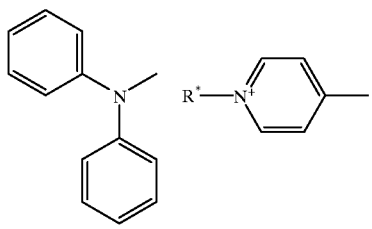

R*=$C_1$–$C_{22}$-alkyl, or —$(CH_2)_x$—$SO_3^-$ where x=2,3 or 4

IIIe) K=L=H and M=Q and are selected from the group consisting of:

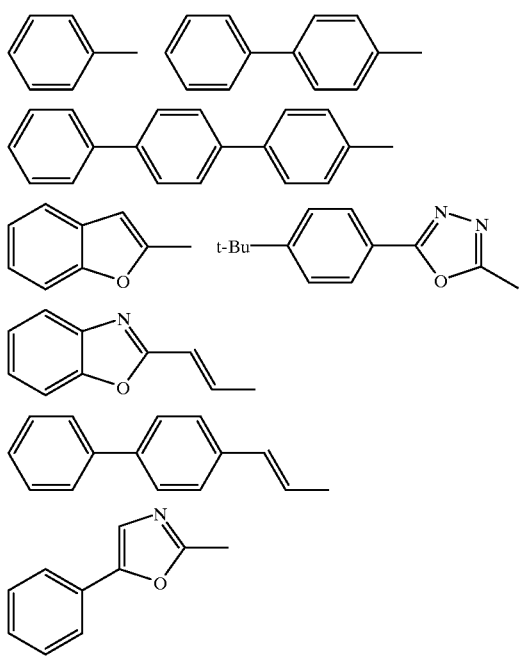

-continued

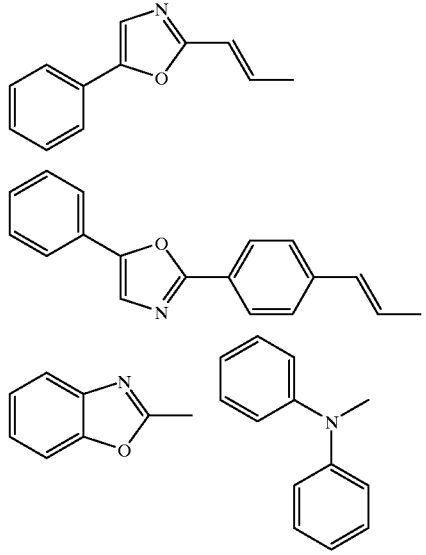

IIIf) K=L and are selected from the group consisting of:

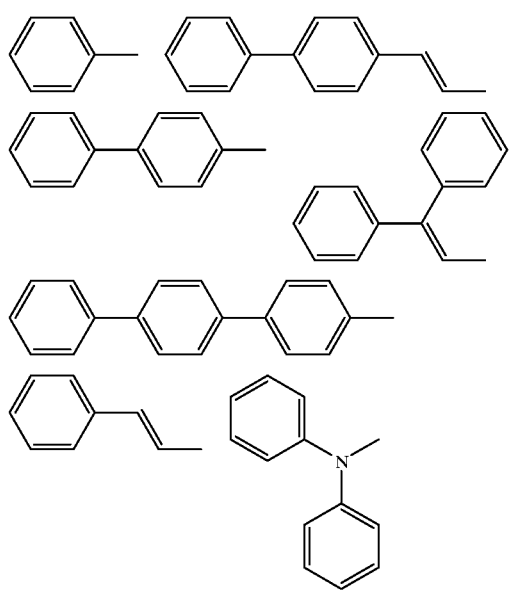

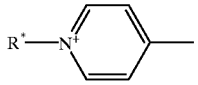

R*=$C_1$–$C_{22}$-alkyl, or —$(CH_2)_x$—$SO_3^-$ where x=2,3 and M=Q and are selected from the group consisting of:

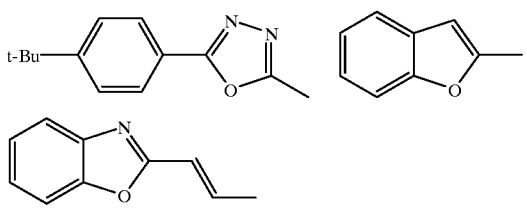

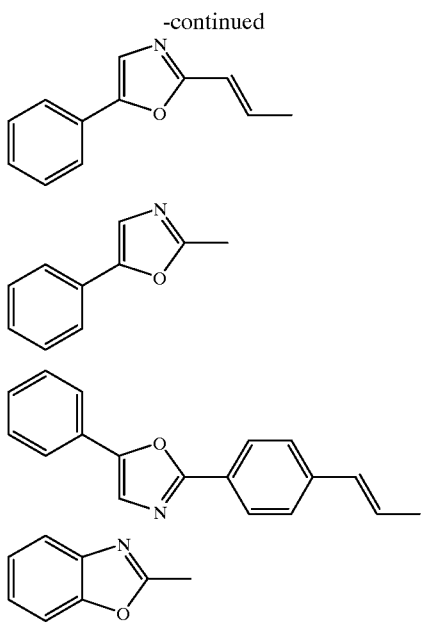

IIIg) K=L and are selected from the group consisting of:

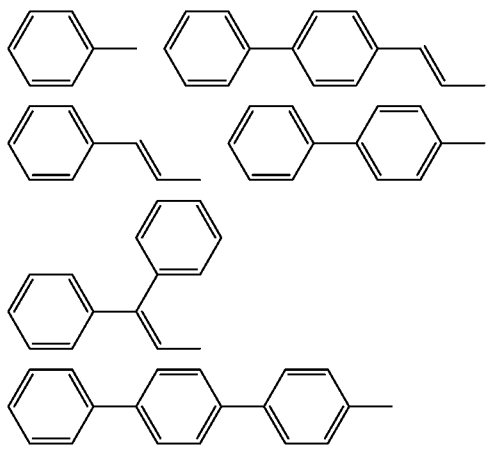

and M=Q and are selected from the group consisting of:

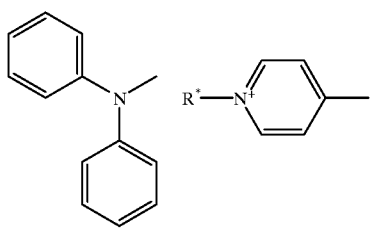

R*=$C_1$-$C_{22}$-alkyl, or —$(CH_2)_x$—$SO_3^-$ where x=2, 3 or 4.

12. An electroluminescence material which comprises one or more hetero-spiro compounds according to claim 10.

13. An electroluminescence device comprising a cothode, one or more active layers and an anode, wherein at least one of the active layers comprises an electroluminescence material according to claim 12.

14. The electroluminescence device according to claim 13, wherein the active layer comprising the electroluminescence material is a light-emitting layer.

15. The electroluminescence device according to claim 13 wherein the active layer comprising the electroluminescence material is a transport layer.

16. The electroluminescence device according to claim 13 wherein the active layer comprising the electroluminescence material is a charge injection layer.

17. A hetero-spiro compound of the formula (IV),

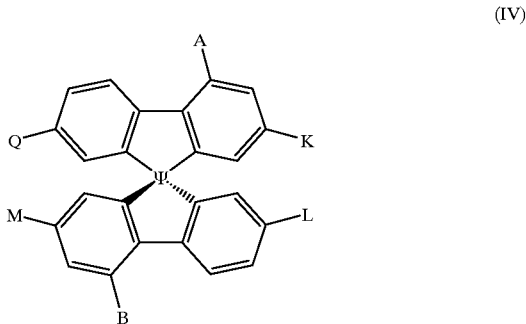

(IV)

where the symbols have the following meanings:
Ψ is Si, Ge or Sn;
A, B, K, L, M, Q, are identical or different and are

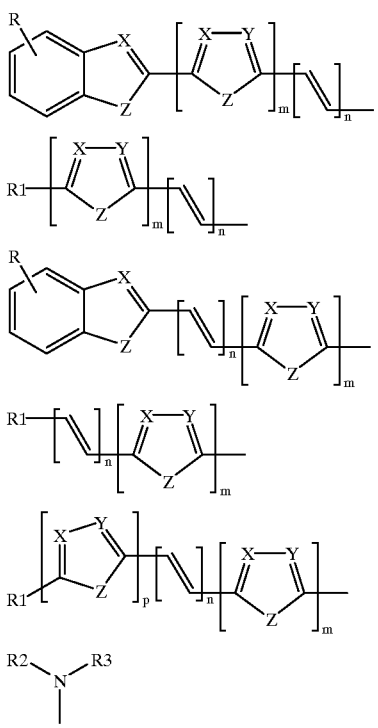

and A, B can also be identical or different and each be a linear or branched alkyl, alkoxy or ester group having from 1 to 22 carbon atoms, —CN, —$NO_2$, —Ar or —O—Ar;

R is —H, a linear or branched alkyl, alkoxy or ester group having from 1 to 22 carbon atoms, —CN, —$NO_2$, —$NR^2R^3$, —Ar or —O—Ar;

Ar is phenyl, biphenyl, 1-naphthyl, 2-naphthyl, 2thienyl, 2-furanyl, where each of these groups can bear one or two radicals R;

m, n, p are, independently of one another, identical or different and are 0, 1, 2 or 3;

x, Y are identical or different and are CR, nitrogen;

Z is —O—, —S—, —NR$^1$—, —CR$^1$R$^4$—, —CH=CH—, —CH=N—;

R$^1$, R$^4$ can be identical or different and have the same meanings as R;

R$^2$, R$^3$ are identical or different and are H, a linear or branched alkyl group having from 1 to 22 carbon atoms, —Ar or 3-methyiphenyl.

18. The hetero-spiro compound according to claim 17, wherein Ψ is Ge or Sn.

19. An electroluminescence material which comprises one or more hetero-spiro compounds according to claim 17.

20. An electroluminescence device comprising a cothode, one or more active layers and an anode, wherein at least one of the active layers comprises an electroluminescence material according to claim 19.

21. The electroluminescence device according to claim 20, wherein the active layer comprising the electroluminescence material is light-emitting layer.

22. The electroluminescence device according to claim 20, wherein the active layer comprising the electroluminescence material is a transport layer.

23. The electroluminescence device according to claim 20, wherein the active layer comprising the electroluminescence material is a charge injection layer.

* * * * *